(12) United States Patent
Bos (10) Patent No.: US 11,123,737 B2
(45) Date of Patent: Sep. 21, 2021

(54) CLOSING ELEMENT FOR CLOSING A CONTAINER FOR SAMPLES FOR ANALYSIS

(71) Applicant: eNose Holding B.V., Zutphen (NL)

(72) Inventor: Albert Bos, Brummen (NL)

(73) Assignee: eNose Holding B.V., Zutphen (NL)

( * ) Notice: Subject to any disclaimer, the term of this patent is extended or adjusted under 35 U.S.C. 154(b) by 0 days.

(21) Appl. No.: 16/101,985

(22) Filed: Aug. 13, 2018

(65) Prior Publication Data

US 2018/0345281 A1 Dec. 6, 2018

Related U.S. Application Data

(63) Continuation of application No. 14/398,169, filed as application No. PCT/NL2013/050325 on May 1, 2013, now Pat. No. 10,046,323.

(30) Foreign Application Priority Data

May 1, 2012 (NL) ...................................... 2008737

(51) Int. Cl.
*B01L 3/00* (2006.01)
*C12Q 1/02* (2006.01)
*G01N 33/497* (2006.01)
*G01N 1/22* (2006.01)

(52) U.S. Cl.
CPC ............ *B01L 3/50825* (2013.01); *C12Q 1/02* (2013.01); *G01N 33/497* (2013.01); *B01L 2200/026* (2013.01); *B01L 2200/0684* (2013.01); *B01L 2300/044* (2013.01); *B01L 2300/048* (2013.01); *G01N 2001/2229* (2013.01); *G01N 2033/4977* (2013.01)

(58) Field of Classification Search
None
See application file for complete search history.

(56) References Cited

U.S. PATENT DOCUMENTS

| 4,057,168 A | * | 11/1977 | Bosshold ........... B65D 51/1644 220/203.17 |
| 4,248,355 A | | 2/1981 | Kolb et al. |
| 4,886,117 A | * | 12/1989 | Patel .................... E21B 33/1243 277/334 |
| 4,886,177 A | | 12/1989 | Foster |
| 5,232,839 A | * | 8/1993 | Eden ....................... C12M 41/46 435/287.4 |

(Continued)

FOREIGN PATENT DOCUMENTS

| EP | 0841094 A2 | * | 5/1998 | ........... B01L 3/50825 |
| EP | 0841094 A2 | | 5/1998 | |

(Continued)

*Primary Examiner* — Matthew D Krcha
(74) *Attorney, Agent, or Firm* — The Webb Law Firm (57) ABSTRACT

The invention relates to a closing element for closing a container for samples for analysis, particularly biological samples. The invention also relates to an assembly of a container and a closing element connected to the container. The invention also relates to a device for analysing samples, particularly biological samples, by making use of an assembly according to the invention. In addition, the invention relates to a method for analysing samples, particularly biological samples, by making use of an assembly according to the invention.

20 Claims, 4 Drawing Sheets

(56) References Cited

U.S. PATENT DOCUMENTS

| | | |
|---|---|---|
| 5,395,589 A | 3/1995 | Nacson |
| 5,894,962 A | 4/1999 | Song et al. |
| 5,932,482 A | 8/1999 | Markelov |
| 6,119,534 A | 9/2000 | Dinsmore |
| 6,652,625 B1 | 11/2003 | Tipler et al. |
| 6,715,624 B2 | 4/2004 | Brockwell |
| 6,903,823 B1 | 6/2005 | Müller et al. |
| 7,387,216 B1 | 6/2008 | Smith |
| 2002/0185186 A1* | 12/2002 | Juliar .................... A61M 39/10 138/96 R |
| 2003/0124506 A1 | 7/2003 | Bedingham et al. |
| 2006/0088943 A1* | 4/2006 | Prohaska ........... G01N 35/1097 436/155 |
| 2007/0272710 A1 | 11/2007 | Bui |
| 2008/0199900 A1 | 8/2008 | Signore et al. |
| 2008/0240990 A1* | 10/2008 | Flaherty ................ B01L 3/5635 422/68.1 |
| 2011/0071055 A1 | 3/2011 | Belgrader et al. |
| 2011/0093207 A1* | 4/2011 | Ingber ...................... B04B 9/14 702/19 |

FOREIGN PATENT DOCUMENTS

| | | |
|---|---|---|
| EP | 0905229 A2 | 3/1999 |
| EP | 1068902 A2 | 1/2001 |
| NL | 2008737 C | 11/2013 |
| WO | 199708337 A1 | 3/1997 |
| WO | 199747729 A1 | 12/1997 |
| WO | 2006013599 A1 | 2/2006 |
| WO | 2007061294 A1 | 5/2007 |
| WO | 2007141255 A1 | 12/2007 |
| WO | WO-2007141255 A1 * | 12/2007 .......... B01L 3/50825 |

* cited by examiner

01
CLOSING ELEMENT FOR CLOSING A CONTAINER FOR SAMPLES FOR ANALYSIS

CROSS-REFERENCE TO RELATED APPLICATIONS

This application is a continuation of U.S. application Ser. No. 14/398,169, filed Oct. 31, 2014, which is the United States national phase of International Application No. PCT/NL2013/050325 filed May 1, 2013, and claims priority to The Netherlands Patent Application No. 2008737 filed May 1, 2012. The disclosure of each of these documents is hereby incorporated in their entirety by reference.

The invention relates to a closing element for closing a container for samples, particularly biological samples. The invention also relates to an assembly of a container and a closing element connected to the container. The invention also relates to a device for analysing samples, particularly biological samples, by making use of an assembly according to the invention. In addition, the invention relates to a method for analysing samples, particularly biological samples, by making use of an assembly according to the invention.

The use of electronic noses makes it possible to determine a composition of gases from which one or more diseases such as asthma, tuberculosis, diabetes, Parkinson's, pneumonia and cancer can be diagnosed. Components (including bacteria) in samples, particularly biological samples, can in addition be identified and/or characterized on the basis of the gas generating metabolism they display. A biological sample, such as for instance a blood, saliva or urine sample, is for this purpose taken from a person, wherein metabolic gas generation will occur in the sample as a result of microbiological activity in the sample, wherein the molecular composition of the formed metabolic gases can be analysed with an electronic nose. The sample is injected here by means of a hollow injection needle into a closed sample bottle. A culture medium is preferably present in this sample bottle. The sample bottle is closed here by means of a cap provided with a septum (rubber disc) through which the injection needle can be placed. Following injection of the sample into the closed sample bottle, a hollow analysis needle will be introduced via the septum into the sample bottle, wherein a space enclosed by the analysis needle is connected to an electronic nose. As a result of diffusion and possible convection flow, metabolic gas formed in the sample bottle will displace via the analysis needle to the electronic nose, where the composition of the metabolic gas can be at least partially determined. Although this virtually new technique provides considerable advantages and options, this technique also has various drawbacks. A significant drawback of the known method is that application of an analysis needle creates the risk of a laboratory technician being injured and possibly infected, which is especially undesirable. In addition, it is recommended that the sample remain as intact as possible after the measurements with the electronic nose, so that optional further analysis with other test equipment is impeded as little as possible.

An object of the invention is to provide an improved component and an improved method enabling relatively safe analysis of biological samples.

The invention provides for this purpose an improved closing element for closing a container for samples, particularly biological samples, comprising: at least one penetrable element enabling injection of a sample via the closing element into a container connected to the closing element, and at least one ventilating channel provided with at least one bacterial filter, which bacterial filter is substantially impermeable to bacteria and is at least permeable to at least one metabolic gas formed in the sample, which ventilating channel is configured for connection to a device for analysing metabolic gas, wherein the at least one ventilating channel is closed in substantially unloaded state by another part of the closing element, in particular a closing body of the closing element, and wherein opening of the ventilating channel takes place by loading at least a part of the closing element. A significant advantage of the closing element according to the invention is that the closing element comprises one or ventilating channels via which (metabolic) gas can displace freely, generally as a result of diffusion and possible convection flow, from the container provided with the biological sample to a space or area outside the container, where the (metabolic) gas can be collected and can be analysed. When a plurality of ventilating channels are applied, it is possible to envisage the ventilating channels debouching into one central (shared) bacterial filter. It is however also possible to envisage each ventilating channel debouching into and/or being provided with its own filter, optionally with its own characteristic filtering action. An additionally applied pressure difference can optionally provide for a more effective displacement of gases. It is thus no longer necessary to have a relatively unhygienic hollow analysis needle pierce the closing element, which is particularly advantageous from the viewpoint of hygiene and safety. Possible cross-contamination between different sample analyses can also be prevented in this way.

Applying one or more gas-permeable bacterial filters, such as a HEPA filter (High Efficiency Particulate Air filter) or a membrane, is advantageous in keeping bacteria present in the biological sample as far as possible in the container so as to prevent contact as far as possible between the bacteria and analysis equipment and/or bystanders The bacterial filter will usually be configured for substantially free passage of gases from the container to the surrounding area and vice versa. The at least one ventilating channel will be positioned at a distance relative to an injection location of the closing element. The at least one ventilating channel will preferably be positioned here at a distance relative to the at least one penetrable element. Creating a mutual distance between the at least one ventilating channel and the injection location can ensure that an injection needle pierces only the penetrable element during injection of a biological sample, and so not by mistake also the ventilating channel and the bacterial filter incorporated therein or co-acting therewith, which would result in undesired leakages via which bacteria could escape from the container. This penetration with an injection needle will take place if it is desired to suction up and use part of the sample for a further analysis following the measurement with the electronic nose. The injection location will generally be positioned substantially centrally, on or close to a longitudinal axis of the closing element, whereby it is advantageous for the penetrable element to be also positioned substantially centrally. The at least one ventilating channel is preferably positioned at a distance from the centre of the closing element, so eccentrically, whereby unintentional penetration of the ventilating channel and/or the bacterial filter can be prevented as far as possible. It is also possible to envisage extracting sample received in the container, generally with use of a hollow needle, from the container via the penetrable element. It is possible to envisage, although this is generally not recommended, injecting the sample into the container and only then providing the container with the closing element according to the invention. If the container is filled in this manner it would be possible to envisage no longer providing the closing element with a penetrable element.

The at least one ventilating channel of the closing element is substantially closed (blocked) when the closing element is at rest and the ventilating channel will be opened as soon as an external pressure (overpressure or underpressure) is exerted on at least a part of the closing element. This external (and/or internal) pressure can for instance be realized by co-action of the closing element with a device for analysing biological samples according to the invention. The advantage of blocking the at least one ventilating channel in unloaded state of (an upper side of) the closing element is that metabolic gases remain conserved as far as possible in the container until the at least one ventilating channel is opened by loading of the closing element. Such a blocking can for instance be realized by applying a pressure-controlled seal or valve forming part of the closing element. An end surface of the at least one ventilating channel preferably connects in substantially unloaded state to substantially another part of the closing element, in particular the closing body, wherein the ventilating channel and the other part of the closing element, in particular the closing body, are displaced relative to each other when at least a part of the closing element is loaded such that opening of the ventilating channel takes place. In this embodiment the closing body does in fact function as a pressure-controlled valve.

The closing element is preferably configured such that the ventilating channel will open after a predefined external pressure has developed, optionally in combination at at least one predefined location on the closing element. Unintentional opening of the ventilating channel can in this way be prevented. It is also possible to envisage the closing element being configured such that the ventilating channel will open once a predefined internal gas pressure has developed, this generally being realized by the development of metabolic gas in the container. A high overpressure in the container can in this way be prevented, this generally being advantageous from a safety viewpoint. In this embodiment the closing element, and particularly the closing body, thus functions as a type of pressure relief valve. In an advantageous embodiment an upper end surface of the at least one ventilating channel is closed in substantially unloaded state by the other part of the closing element, in particular the closing body. Such an orientation implies that the ventilating channel is positioned under the closing body and preferably enclosed by the closing body, whereby the ventilating channel can be screened relatively well from the surrounding area, whereby contamination of the ventilating channel with molecules from the surrounding area can be prevented as well as contamination of the surrounding area with molecules from the ventilating channel. This generally enhances the accuracy, and thereby the quality of the analysis of metabolic gases to be performed.

The closing body usually takes a cap-like form. A closing body comprises for this purpose a generally cylindrical peripheral wall, optionally provided with for instance screw thread and/or bayonet closure, and an upper wall. The closing body, particularly an upper wall thereof, is preferably provided with at least one analysis opening configured for connection to a device for analysing metabolic gas. The analysis opening will generally also be used to at least partially expose the penetrable element, whereby the sample can be injected quickly and efficiently. Metabolic gas developed in the sample will accumulate at least partially as headspace (gas phase/vapour phase) above the sample. These metabolic gases for analysis can be discharged via the ventilating channel and subsequently via the analysis opening in the direction of the analysis device. It is advantageous here that the analysis opening of the closing body and the ventilating channel do not lie in line. This preferably implies not only that the respective axes of the ventilating channel and the analysis opening do not coincide (lie out of line), but also that the two openings do not overlap each other, whereby the metabolic gases can only leave the closing element via a non-linear path. Such an orientation generally facilitates the ability to selectively block and open the ventilating channel.

The bacterial filter is preferably incorporated into the ventilating channel. The bacterial filter is preferably closed all around here by at least one channel wall of the ventilating channel. The bacterial filter can in this way be screened and held in position relatively well, which generally enhances the filtering action of the closing element as such.

In a preferred embodiment of the closing element according to the invention the penetrable element is formed by a septum connected to another part of the closing element. The end surfaces of the septum will be at least partially clear here, whereby the septum forms a part of the upper surface and a part of the lower surface of the closing element. The septum is manufactured from an elastic material which can be pierced relatively easily with an injection needle. After removal of the injection needle from the septum, the septum will close again in substantially medium-tight manner. A suitable type of material for the manufacture of the septum is an elastomer, in particular rubber. The septum can here form a separate element connected by means of welding, glueing or clamping to another part of the closing element. It is however also possible to envisage the septum forming an integral part of the closing element which can be manufactured substantially wholly from an elastic material. It is possible to envisage the penetrable element being formed by a weakened portion of the closing element. A weakened portion is particularly understood to mean a part with a small material thickness, this facilitating piercing by an injection needle. It is also possible to envisage the weakened portion having the same material thickness as adjacent parts, but wherein the weakened portion is weakened by for instance micro-perforations arranged by means of a laser. In this embodiment the weakened portion can also form an integral part of the closing element as such. The weakened portion is however more preferably manufactured here from an elastic material, in particular an elastomer, whereby the weakened portion could also be deemed as septum.

As stated above, the bacterial filter can be formed by a HEPA filter. In an alternative preferred embodiment the bacterial filter is formed by a membrane. The membrane will generally be easy to position in or on a ventilating channel. The membrane can here optionally take a somewhat flexible form, which can facilitate attachment of the membrane. The membrane can optionally be of selective nature here, and can for instance be configured to block—in addition to bacteria and/or proteins—one or more specific gaseous molecules, such as for instance carbon dioxide, wherein other gaseous molecules would be able to pass through the membrane. This separation can take place on the basis of for instance molecule size and/or polarity. It is possible in this way to allow only the molecules characteristic of a clinical picture to pass through the membrane, which can considerably enhance the final sample analysis. Each bacterial filter will generally be provided with pores (microchannels). In order to have as many bacteria as possible blocked by the bacterial filter, it is advantageous for the bacterial filter to comprise pores with a maximum diameter of 45 micron. The diameter of the at least one ventilating channel preferably lies between 0.5 and 50 millimetres, more preferably between 0.5 and 10 millimetres, in particular between 1 and 5 millimetres. The bacterial filter can be positioned here at least partially in the ventilating channel. It is also possible to envisage the bacterial filter closing an outer end of the ventilating channel. The bacterial filter and the ventilating channel generally connect substantially medium-tightly to each other in order to preclude the possibility of (metabolic) gas or bacteria passing through the closing element while bypassing the bacterial filter. It is otherwise possible to envisage the closing element comprising a plurality of ventilating channels, wherein each ventilating channel is provided with at least one bacterial filter, which can for instance be advantageous for purposes of analysis. Applying a plurality of ventilating channels makes it possible for instance to perform several similar or different analyses separately of each other for a single biological sample.

The closing element is preferably configured to at least partially enclose (engage round) the container. The closing element will in this way function as cap for the container. It is however also possible to envisage giving the closing element a form such that it is configured to be at least partially received in the container. The closing element will in this way function mainly as a stopper. It is also possible to envisage giving the closing element a form such that the closing element is configured to grip round the container and to protrude into the container (neck).

The closing element can here be clamped in or round the container. However, in order to realize a more secure coupling of the closing element relative to the container, it is advantageous for the closing element to comprise coupling means for coupling the closing element to the container. The coupling means are generally configured here for co-action with counter-coupling means forming part of the container. The coupling means are preferably formed by screw thread for realizing a screw thread connection. It is also possible to envisage the coupling means being configured to realize a bayonet closure or snap connection.

In an embodiment of the closing element according to the invention the closing or opening of the ventilating channel is not necessarily selective. Such a closing element for closing a container for samples for analysis, particularly biological samples, comprises: at least one penetrable element for injecting a sample via the closing element into a container connected to the closing element, and at least one ventilating channel provided with at least one bacterial filter, which bacterial filter is substantially impermeable to bacteria and at least permeable to at least one metabolic gas formed in the biological sample, which ventilating channel is configured for connection to a device for analysing metabolic gas. The above stated embodiment is also described in the Netherlands priority application NL2008737, the content of which forms part of the description of this patent specification by way of reference.

The invention also relates to an assembly of a container for a sample, particularly a biological sample, and a closing element according to the invention connected to the container. The container will be formed here by a flask or bottle. The container will usually comprise a container body and a container neck connected to the container body, wherein the closing element is generally connected to the container neck. The container is usually manufactured from a light-transmitting material such as plastic or glass, so that the content of the container is visible at a glance. It is moreover possible in this way to optically measure the pH of the biological sample in relatively simple manner. The closing element is generally manufactured substantially from plastic. The biological sample can be a human sample, an animal sample or a vegetable sample. Non-biological samples on which bacterial growth takes place could optionally also be arranged in the assembly according to the invention for analysis purposes.

The invention further relates to an (interrelated) device for analysing biological samples by making use of at least one assembly according to the invention, comprising: at least one support structure for supporting at least one assembly of a container provided with a biological sample and a closing element connected to the container, at least one top structure connected or connectable to the support structure, wherein the top structure comprises at least one analysis compartment, which analysis compartment is configured for substantially medium-tight connection to at least one ventilating channel of the closing element of the assembly, and wherein the analysis compartment comprises at least one chemical trace detector for detecting at least one metabolic gas formed in the biological sample. The top structure, in particular the analysis compartment, is preferably configured to load (exert pressure on) the closing element of the assembly such that the ventilating channel will be opened as a result and displacement of metabolic gas in the direction of the analysis compartment can take place. Advantages of this selective opening of the ventilating channel have already been discussed in the foregoing. Having the analysis channel connect in substantially medium-tight manner to an outer side of the closing element so that the analysis compartment is in communicative connection with at least one ventilating channel enables metabolic gas, discharged as a result of diffusion and/or convection flow, to be guided via the ventilating channel to the chemical trace detector for purposes of analysis. Neither the closing element nor the container need be penetrated here by the device. In order to realize the substantially medium-tight closure it is advantageous for the top structure to engage under bias on the at least one closing element, preferably via at least one sealing element. The chemical trace detector in fact forms an electronic nose for detecting characteristic metabolic gases or combinations of gases which are usually formed in small quantities (traces) in the biological sample. These metabolic gases consist generally of volatile organic compounds (voc). The electronic nose can be of diverse nature, construction and operation. Use is however preferably made of a chemical trace detector configured to allow reaction (oxidizing or reduction) of at least one or more metabolic compounds, this resulting in a detectable, characteristic, temperature-dependent resistance change in the trace detector. The chemical trace detector preferably comprises for this purpose at least one semi-conducting sensor, at least one heating element for heating the semi-conducting sensor, at least one processor for controlling the heating element and a detection circuit for detecting the change in resistance of the semi-conducting sensor which is at least partially determined by the presence of at least one chemical trace which reacts in the presence of the semi-conducting sensor. Heating the semi-conducting sensor will initiate redox reactions on or close to the sensor with one or more metabolic products as reactant, which results in a detectable, characteristic, usually temperature-dependent change in resistance of the semi-conducting sensor. In order to stimulate the occurrence of—a determined type of—redox reaction(s) a catalyst, usually manufactured from platinum or palladium, can optionally be arranged on or in the semi-conducting sensor. The semi-conducting sensor is preferably manufactured here from a semi-conductor, more preferably a metal oxide (MOS), in particular tin oxide, zinc oxide, iron oxide, tungsten oxide and/or cesium oxide. The material of the sensor is preferably manufactured from a sintered granular material, more preferably with semi-conductor properties. Applying a sintered granular material generally increases the effective sensor surface area and creates grain boundary transitions, this enhancing the sensitivity of the sensor. At higher temperatures redox reactions take place with oxygen which is adsorbed to the sensor surface and which, depending on the temperature, can be present in different forms. In some cases it is also possible for a chemical trace, without the adsorbed oxygen, to itself undergo a redox reaction on the sensor surface, in particular the metal oxide surface. Both oxidation and reduction are therefore possible on the sensor surface. Measurable redox reactions take place substantially always on the surface (crystal lattice) and substantially not in the vicinity thereof. Chemical reactions with reactive particles, such as for instance desorbed radicals, could possibly take place above the sensor surface, although if no electrons are exchanged with a crystal lattice of the (semi-)conducting sensor it will generally not then be possible to measure a change in resistance of the sensor. Chemical traces will thus usually first adsorb to the sensor surface, after which the chemical traces will react, followed by desorption of the reaction products. The detected temperature-dependent change in resistance is here the result of all chemical reactions taking place on the sensor surface at a determined temperature. The presence of one or more characteristic chemical traces or groups of chemical traces in the sample results in a (known) characteristic contribution toward the resistance change at a pre-known temperature. By measuring the resistance change at different temperatures a temperature-dependent pattern of resistance change is obtained which can be compared to one or more stored reference patterns, on the basis of which it is possible to determine relatively precisely which characteristic chemical traces are present in the sample. The sensor as such can take a substantially plate-like form, which generally facilitates heating of the sensor by means of the heating element. The heating element is configured to heat the semi-conducting sensor to a typical temperature of between 200° C. and 600° C. It is important here to be able to precisely regulate the temperature of the heating element since the temperature usually determines the type of chemical compound (chemical trace) which reacts on the sensor surface, and is thereby related to a measured characteristic change in resistance of the sensor. The heating element will generally be of electrical nature and comprise one or more electrical resistor tracks or a Peltier element. The processor is preferably configured here to regulate the specific resistance, and thereby the temperature, of the one or more resistor tracks. A further advantage of the applied chemical trace detector is that the detector is relatively insensitive to fluctuations in temperature and air humidity, this enhancing the applicability of the chemical trace detector. The heating element is configured to heat the semi-conducting sensor to a typical temperature of between 200° C. and 600° C. A suitable sensor is described in WO 2007/061294, the content of which forms part of this patent specification by way of reference. The advantage of this specific type of trace detector (sensor) for the analysis is that it can take a relatively compact form and that sample analyses can be performed in relatively accurate and reproducible manner. The analysis compartment will usually take a channel-like form.

In a preferred embodiment the processor of the chemical trace detector is configured to determine at least a part of the composition of the gas mixture coming from the tested sample on the basis of the resistance change detected by the detection circuit. Comparing the detected resistance profile (resistance pattern) to a resistance profile, or information related thereto, prestored on a storage medium, generally in a database, makes it possible to determine on the basis of profile comparison and pattern recognition whether one or more characteristic chemical traces do or do not occur in the tested sample. During detection of the presence of a characteristic chemical compound or group of compounds in the tested sample an auditive and/or visual signal can be generated by a signal-generating element coupled to the processor. It is also possible to envisage a signal being generated by the signal-generating element after every measurement, but wherein the nature of the signal depends on the analysis results. The signal has the purpose of alerting the lab technician to the presence or absence of one or more characteristic traces in the tested sample. It is also possible to envisage the measured signals being presented graphically, preferably on a screen. Information about components present in the sample can be derived from the form of the displayed signals.

The support structure is preferably configured to substantially wholly enclose at least the container of the at least one assembly. The support structure is provided here with one or more receiving spaces for the assembly. It is possible to envisage a single receiving space being suitable for accommodating multiple assemblies simultaneously. Through the use of one or more receiving spaces the support structure in fact forms a housing for the assemblies, wherein at least the containers of the assemblies are at least partially enclosed. The support structure is preferably manufactured here from a material which blocks ultraviolet ambient radiation so that degradation of the biological sample can be prevented. The top structure is preferably embodied as a cover so as to enable the at least one assembly to be wholly enclosed by the device. The top structure will usually be pivotally connected here to the support structure. It is however also possible to envisage the top structure being releasably connected to the support structure so that the top structure can be completely removed when at least one assembly is placed in or on the support structure. Following placing of the at least one assembly, the top structure can be attached to the support structure and preferably be locked relative to the support structure. The above described support structure and components thereof can be deemed as a unit. It is also possible to envisage coupling a number of units to each other in optionally releasable manner, whereby a modular system is generated. It is in this way possible to analyse a larger number of samples at the same time with one system.

The top structure, particularly the at least one sealing element, is preferably configured to engage substantially medium-tightly on a closing body of the closing element around an analysis opening arranged in the closing body. After opening of the ventilating channel, the analysis opening is connected to the ventilating channel, whereby the metabolic gas for analysis can be guided relatively quickly and efficiently into the analysis device, wherein the risk of metabolic gas escaping is minimized.

In a preferred embodiment the device comprises at least one heating element for heating the biological sample received in at least one container. Heating the biological sample to a typical temperature of about 37° C. has the advantage that the metabolic activity and the replication speed of micro-organisms (bacteria) present in the biological sample is increased considerably, whereby the final analysis time can be considerably reduced. At this increased temperature the analysis time is generally between 4 hours and 5 days, depending on the type of bacterium. Positioning the heating element in the top structure has a two-fold advantage. A significant advantage is that the heat is in this way generated at a distance from the sample, whereby the sample temperature can be regulated relatively well and overheating of the sample can be prevented. For the purpose of distributing the generated heat inside the device in the direction of the container and the sample received therein it is advantageous for the device to comprise at least one fan.

In an advantageous embodiment variant the sample is kept in motion in the device. This movement can be continuous or discontinuous. The movement is preferably realized by vibrating, moving or shaking the assembly or via a magnetic element which is added to the container or arranged in the sample and is kept in motion via an external magnet. The support structure can comprise at least one turbulence-generating element here for causing shaking and/or vibration of the at least one assembly. Keeping the sample in motion can considerably increase the metabolic activity and the replication speed of the bacteria in the sample, which can considerably enhance the final qualitative analysis.

In a preferred embodiment the device comprises at least one preconcentrator for temporarily binding by means of adsorption one or more gas components coming from the sample. The preconcentrator will generally be arranged here in the analysis compartment. Once the analysis compartment has been exposed for a sufficient length of time to a gas mixture from the sample, the gas components present on or in the preconcentrator are released therefrom by means of heating and, preferably via a pump system, guided along the at least one chemical trace detector. The preconcentrator can be cleaned after use by removing components which may still be bound thereto. Use is preferably made here of the circulating system which draws in and guides optionally purified ambient air through or along the preconcentrator. The preconcentrator can optionally be heated here to enable improved cleaning.

The device preferably takes a mobile, in particular portable, form, whereby it is relatively easy to displace the device to a suitable location or destination. The mobile character of the device can considerably increase the applicability of the device. When the device comprises at least one electrical energy source which is at least coupled to the at least one chemical trace detector, the device can function fully autonomously, which is particularly advantageous. This can provide further advantage particularly in less developed countries because a mains supply is not usually available, or available to a limited extent.

The invention also relates to a method for analysing biological samples by making use of an assembly according to the invention, and particularly by also making use of the device according to the invention, comprising of: A) providing an assembly of a container and a closing element connected to the container, B) injecting a biological sample via the at least one penetrable element of the closing element into the container, C) having the at least one ventilating channel of the closing element connect in substantially medium-tight manner to at least an analysis compartment provided with at least one chemical trace detector, D) allowing metabolic gas formed in the container to displace via the ventilating channel and the bacterial filter of the closing element into the analysis compartment, and E) at least partially analysing the metabolic gas in the analysis compartment with at least one chemical trace detector. In order to shorten the analysis time it is advantageous for the method to comprise step F), comprising of heating and/or keeping in motion for a period of time the biological sample injected into the container. Further advantages and embodiment variants have already been described at length in the foregoing.

The invention will be elucidated on the basis of the non-limitative exemplary embodiments shown in the following figures. Herein.

Figure 1:
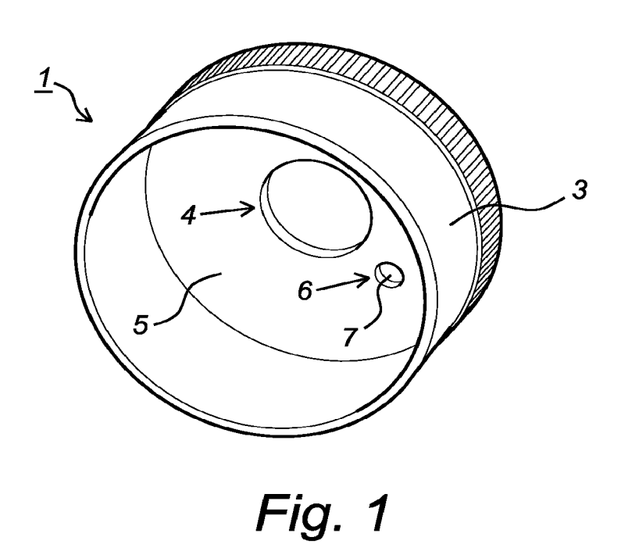
FIG. 1 is a perspective bottom view of a closing element according to the invention.

FIG. 1 is a perspective bottom view of a closing element 1 according to the invention. Closing element 1 is configured to be arranged on a container 2 for holding a biological (human or animal or vegetable) sample (see FIG. 2), wherein container 2 is partially enclosed by closing element 1. Closing element 1 here comprises a cap-like closing body 3 provided with a central (analysis) opening 4 which in practice will not be visible in the view according to FIG. 1 but is nevertheless drawn for the sake of completeness. Closing body 3 will generally be manufactured from plastic or metal. Central opening 4 is closed by a septum 5 which is manufactured from an elastomer and enclosed by closing body 3. Septum 5 is provided with a ventilating channel 6 provided with a membrane 7. Membrane 7 functions as bacterial filter, wherein bacteria cannot pass through membrane 7, while gas can pass through membrane 7 relatively unhindered. On a peripheral side the membrane 7 connects closely to an inner wall of ventilating channel 6 so that gas can only pass through ventilating channel 6 via membrane 7. A lower outer end of ventilating channel 6 is clear and in assembled state (see FIG. 2) is in open contact with an atmosphere enclosed by container 2. In unloaded state (rest position) an upper outer end of ventilating channel 6 connects to closing body 3. The upper outer end of ventilating channel 6 can be opened by exerting an (axial) pressure on septum 5 in a direction away from closing body 3 (see FIG. 4), after which gas present in container 2 can leave the container substantially unhindered via ventilating channel 6. Displacement of gas from container 2 via ventilating channel 6 to an area outside container 2 generally takes place relatively quickly as a result of diffusion. The gas displacement can be reinforced by heating gas present in container 2, whereby a convection flow will be set into motion, or by applying a pressure difference over membrane 7 by means of an additional pump, wherein an underpressure is applied outside the assembly of closing element 1 and container 2 whereby accelerated diffusion is forced. Container 2 is formed in this exemplary embodiment by a plastic or glass sample bottle with a typical volume of between 20 and 100 millilitres. Container 2 is particularly configured to hold a biological sample of a human, an animal or a plant. Metabolism will occur in or on the sample due to microbiological activity in the sample, which results in metabolic gas formation. The composition of this metabolic gas formation can be characteristic for the presence of a disease from which the person or animal in question is suffering, or for a bacterium, parasite or fungus. Applying the particular closing element 1 can allow the gases formed in container 2 to leave the assembly of closing element 1 and container 2 in relatively simple manner so that the composition of said gases can be determined by means of an electronic nose, in particular a chemical trace detector comprising one or more metal oxide sensors (semi-conducting sensors), without having to penetrate the assembly of container 2 and closing element 1, for instance by means of an analysis needle. This is particularly advantageous from a hygiene and safety viewpoint.

Figure 3:
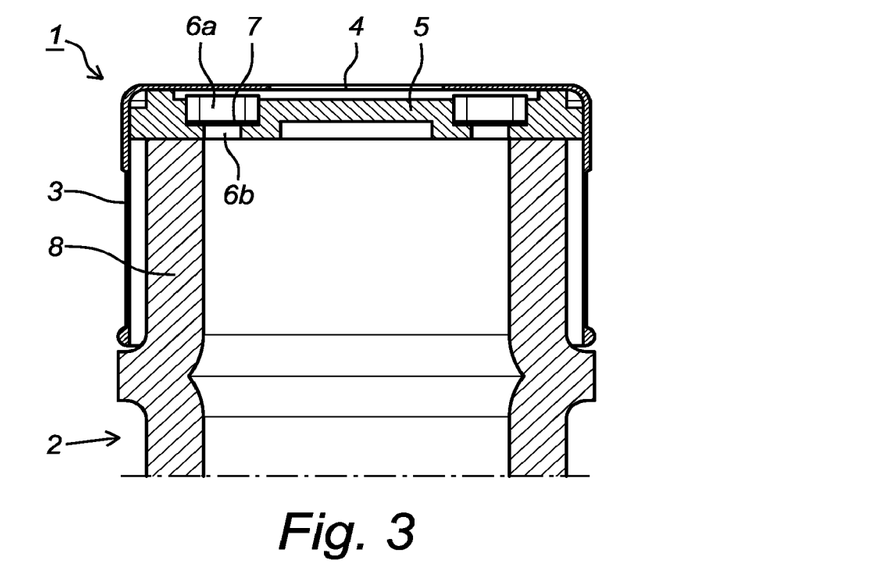
FIG. 3 shows a cross-section of an upper part of the assembly according to FIG. 2.
Figure 4:
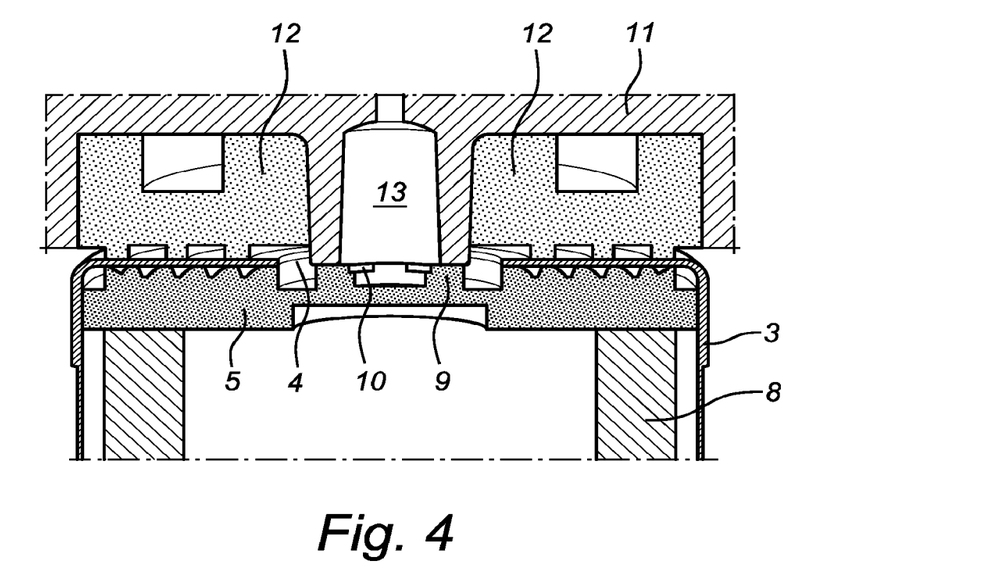
FIG. 4 shows another cross-section of an upper part of the assembly according to FIGS. 2 and 3.

FIG. 3 shows that closing body 3 connects closely to a neck 8 of container 2. Also shown is that septum 5 is clamped between closing body 3 and an upper side of neck 8 of container 2. The eccentrically positioned ventilating channel 6 has a variable diameter, wherein the upper outer end 6a of ventilating channel 6 is wider than the lower outer end 6b of ventilating channel 6. Septum 5 has an internal diameter substantially identical to an external diameter of the upper outer end 6a of ventilating channel 6, whereby septum 5 fits closely onto an inner wall of the upper outer end 6a of ventilating channel 6 and wherein septum 5 is supported by the narrower lower outer end 6b of ventilating channel 6. Further shown clearly in FIG. 3 is that upper outer end 6b of ventilating channel 6 connects in the shown unloaded state to an inner side of closing body 3. Shown in more detail in the cross-section according to FIG. 4 is that in unloaded state around central opening 4 the septum 5 connects substantially gas-tightly to an inner side of closing body 3. A central part of septum 5 lying in line with central opening 4 of closing body 3 is provided with an upright bush 9 provided with a plurality of passage slots 10, whereby a crenellated structure is obtained. An analysis device 11 for analysing metabolic gases formed in the sample received in container 2 will generally engage medium-tightly on an upper side of closing body 3 by applying a sealing element 12. Sealing element 12 here encloses an analysis compartment 13, a lower outer end of which is configured for co-action with the upright bush 9 of septum 5 such that analysis compartment 13 presses the bush in downward direction to some extent (in the direction of container 2), whereby the seal between septum 5 and closing body 3 is released, after which gas formed in container 5 can displace substantially freely via ventilating channel 6 (not shown in FIG. 4) and via passage slots 10 into analysis compartment 13, where the actual analysis of the composition of the received gases can be performed.

Figure 2:
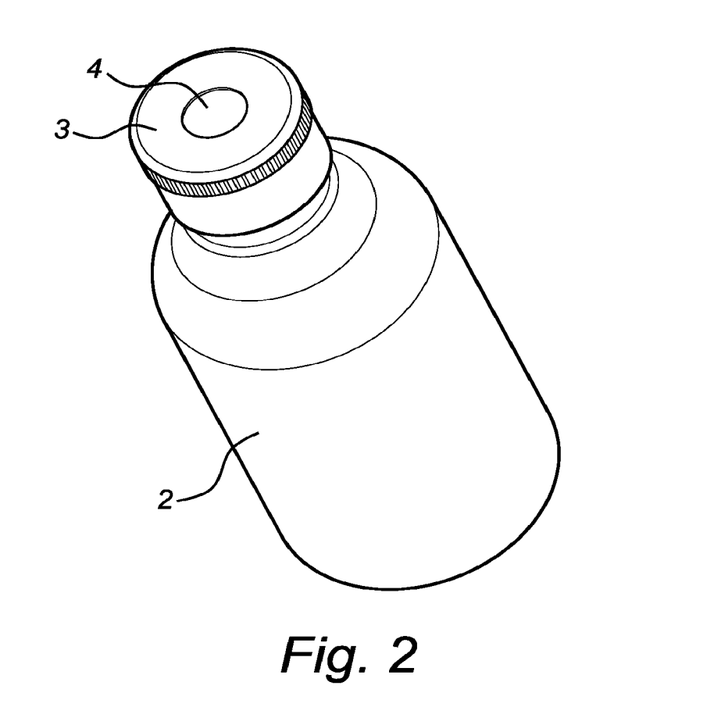
FIG. 2 is a perspective view of an assembly of a container for a biological sample and the closing element according to FIG. 1 connected to the container.
Figure 5:
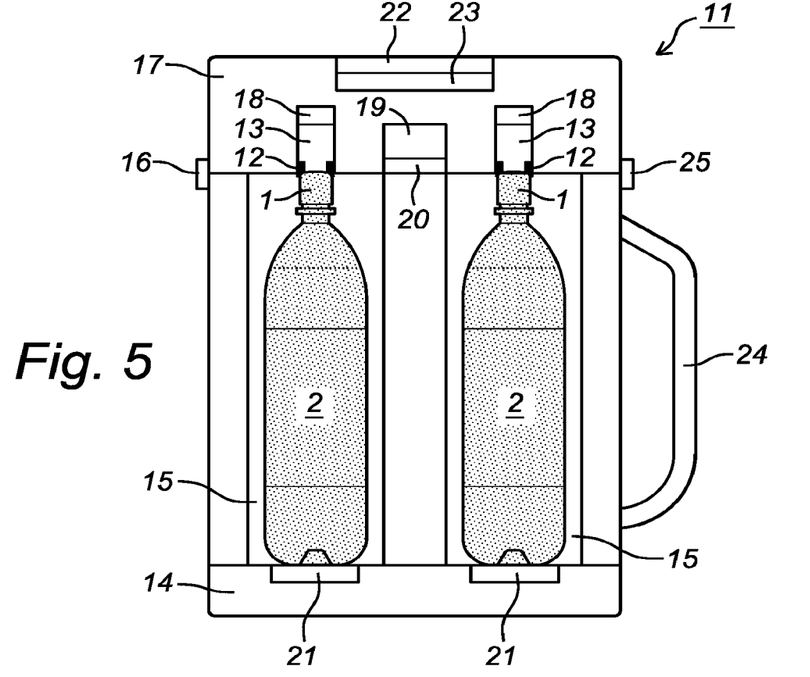
FIG. 5 shows a schematic cross-section of a device for analysing biological samples in which multiple assemblies according to FIGS. 2-4 are received.
Figure 6:
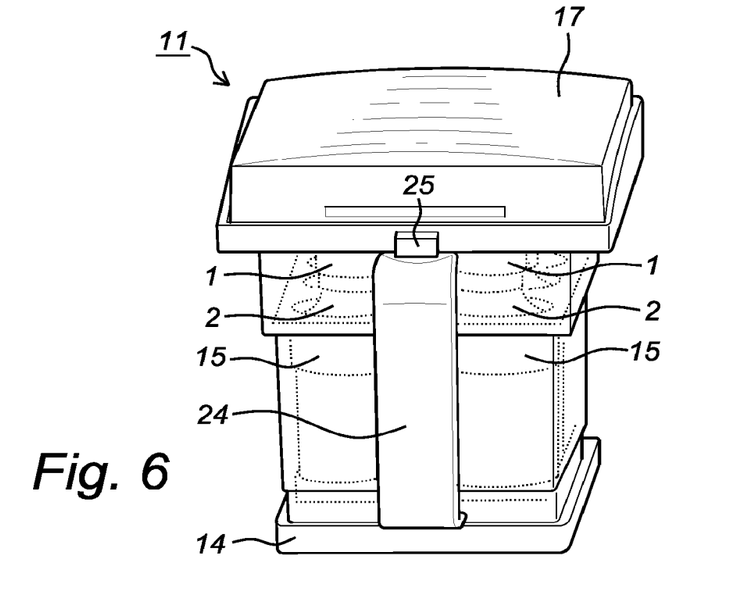
FIG. 6 is a perspective, cut-away view of the device according to FIG. 5.

FIG. 5 shows a schematic cross-section hereof and FIG. 6 shows a transparent perspective view of a portable device 11 for analysing biological sample in which multiple assemblies according to FIGS. 2-4 are received. Device 11 comprises a support structure 14 configured as housing for four assemblies of a container 2 provided with biological sample and a closing element 1 mounted thereon. Support structure 14 comprises for this purpose four receiving spaces 15 which are sufficiently large to accommodate the assemblies 2. Device 11 further comprises a top structure 17 pivotally connected to support structure 14 by means of a hinge 16. Top structure 17 functions here as cover, using which the receiving spaces 15 can be substantially fully closed. Top structure 17 can optionally be coupled releasably to support structure 14. It is possible here to envisage connecting top structure 17 to support structure 14 in other manner, for instance by means of a bayonet closure, so that top structure 17 can engage under bias on support structure 14, and thereby on assemblies 2, which generally enhances the sealing capacity of device 11. Top structure 17 comprises a plurality of analysis compartments 13, wherein each analysis compartment 13 is configured to connect to an upper side of a closing element of an assembly. Each analysis compartment 13 is surrounded here by a sealing element 12 for the purpose of realizing a medium-tight closure between top structure 17 and each closing element 1. A chemical trace detector 18 is positioned in each analysis compartment 13 for the purpose of analysing metabolic gases vented from container 2 via closing element 1. Device 11 further comprises a heating element 19 and a fan 20 for respectively heating and spreading heat in the receiving spaces so that the biological samples are heated to a temperature of preferably between 35 and 40 degrees Celsius. In this exemplary embodiment a shaker plate 21 is provided at the bottom of each receiving space 15 of support structure 14 for the purpose of keeping the biological samples in motion, this usually enhancing the microbiological activity. Device 11 can optionally be shaken by external shaking equipment. A battery 22 incorporated into top structure 17 ensures that sufficient electrical energy is supplied for performing the measurements and optionally controlling heating element 19. Alternatively, device 11 can also be connected to the mains supply. A central processor 23 provides for control of the electrical components of device 11. Device 11 is provided with a handle 24 in order to facilitate carrying of device 11. Top structure 17 is preferably pivotable relative to support structure 14 between an opened position, in which the assemblies can be placed in or removed from support structure 14 in relatively simple manner, and a (shown) closed position in which the assemblies are enclosed by device 11 in substantially medium-tight (gas and liquid-tight) manner. In the shown situation it can be advantageous to lock top structure 17 relative to support structure 14 by means of a locking element 25. Multiple samples present in the plurality of assemblies 2 can be analysed simultaneously by means of device 11.

Figure 7:
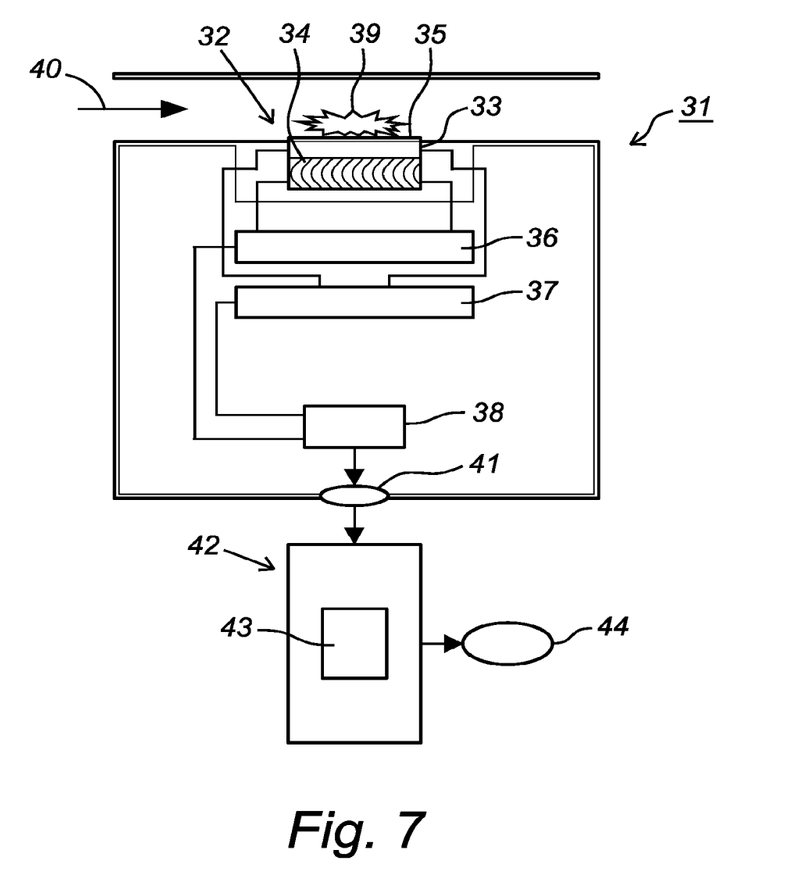
FIG. 7 is a schematic view of a chemical trace detector for use in the device according to FIGS. 5 and 6.

FIG. 7 is a schematic view of a chemical trace detector 31 for use in the device according to FIGS. 5 and 6. Detector 31 comprises here a heatable semi-conducting sensor 32, also referred to as hotplate sensor. Semi-conducting sensor 32 preferably comprises a (semi-conducting) metal oxide layer 33 which is sensitive to chemical (redox) reactions taking place in the immediate vicinity, and a heating element 34 for heating the metal oxide layer 33. The metal oxide layer 33 exhibits a temperature-dependent change in resistance subject to chemical traces which react on or close to a free surface 35 of the metal oxide layer 33. Heating element 34 is preferably mounted on or close to the metal oxide layer 33 and is preferably manufactured by means of Micro-Electrical Mechanical Systems (MEMS) technology, so that the temperature of the metal oxide layer 33 will be substantially identical to the temperature of heating element 34. Heating element 34 has a low thermal mass and is controlled by a processor 36 for the purpose of realizing a stable temperature in the metal oxide layer 33. This is usually achieved by applying a separate electronic circuit provided with one or more Wheatstone bridges. The metal oxide layer 33 is coupled to a detection circuit 37 for detecting the temperature-dependent resistance change resulting from the presence of one or more chemical traces or groups of chemical traces which react on or close to the (heated) semi-conducting sensor 32. The values measured by detection circuit 37 are stored on an internal memory 38 such as a flash memory or other type of memory. One or more detected resistance values are stored in internal memory 38 as cross-reference to one or more predefined temperatures, so that a footprint of the gas mixture with one or more characteristic chemical compounds 39 therein is generated which is related to the gas mixture from the sample. The information stored in memory 38 is compared via a communication connection 41 to a database 43 stored on a storage medium 42 and provided with predefined footprints for known gas mixtures with one or more characteristic chemical compounds therein. Storage medium 42 and the associated database 43 can be wholly incorporated into the device according to the invention, wherein communication connection 41 takes place in fully wired manner. In an alternative preferred embodiment the storage medium 42 is present at a different location and communication connection 41 preferably takes place wirelessly. Comparing the detected footprint to the footprint(s) stored in database 43 makes it possible to determine whether there is a 'best match' 44 and to determine the presence of one or more characteristic chemical compounds in the biological sample. The comparison and identification of footprints takes place here by means of known pattern recognition and identification software.

It will be apparent that the invention is not limited to the exemplary embodiments shown and described here, but that within the scope of the appended claims numerous variants are possible which will be self-evident to the skilled person in the field.

The inventive concepts described in the foregoing are illustrated on the basis of several illustrative embodiments. It is possible to envisage individual inventive concepts being applied without also applying other details of the described embodiment. It is not necessary to elaborate examples of all conceivable combinations of the above described inventive concepts, since a skilled person will appreciate that multiple inventive concepts can be (re)combined so as to arrive at a specific application.

The invention claimed is:

1. A closing element for closing a container for biological samples for analysis comprising:
    at least one penetrable element for injecting a sample therethrough via the closing element into a container connected to the closing element, and
    at least one ventilating channel provided with at least one bacterial filter, which bacterial filter is substantially impermeable to bacteria and is at least permeable to at least one metabolic gas formed in the biological sample, which the ventilating channel is configured for connection to a device for analysing metabolic gas,
    wherein the at least one ventilating channel is positioned at a distance from the at least one penetrable element, wherein the at least one ventilating channel and the at least one penetrable element are mutually eccentrically positioned at a distance from each other, wherein the at least one ventilating channel is closed in a substantially unloaded state by a closing body of the closing element, and wherein opening of the at least one ventilating channel takes place by loading at least a part of the closing element with external axial pressure.

2. The closing element as claimed in claim 1, wherein an end surface of the at least one ventilating channel connects in substantially unloaded state to substantially another part of the closing element, and wherein the ventilating channel and the other part of the closing element are displaced relative to each other when at least a part of the closing element is loaded such that opening of the ventilating channel takes place.

3. The closing element as claimed in claim 1, wherein the closing element is configured such that the closing element will open once a predefined gas pressure has developed in the container.

4. The closing element as claimed in claim 1, wherein an upper end surface of the at least one ventilating channel is closed in a substantially unloaded state by the closing body.

5. The closing element as claimed in claim 1, wherein the bacterial filter is incorporated into the ventilating channel.

6. The closing element as claimed in claim 1, wherein the bacterial filter is formed by a membrane or HEPA filter.

7. The closing element as claimed in claim 1, wherein the closing element comprises a plurality of ventilating channels, wherein each ventilating channel is provided with at least one bacterial filter.

8. A system for analysing samples by making use of at least one assembly of a container for a biological sample and comprising the closing element as claimed in claim 1 connected to the container, the system further comprising:
    at least one support structure for supporting at least one assembly of a container provided with a biological sample and a closing element connected to the container,
    at least one top structure connected to the support structure, wherein the top structure comprises at least one analysis compartment, which analysis compartment is configured for substantially medium-tight connection to at least one ventilating channel of the closing element of the assembly, and wherein the analysis compartment comprises at least one chemical trace detector for detecting at least one metabolic gas or composition of gases formed in the biological sample,
    wherein the top structure is configured to load the closing element of the assembly such that the ventilating channel will be opened as a result and displacement of metabolic gas in the direction of the analysis compartment can take place.

9. The system as claimed in claim 8, wherein the device is configured for simultaneous co-action with a plurality of assemblies.

10. The system as claimed in claim 8, wherein the top structure is releasably, connected to the support structure.

11. The system as claimed in claim 8, wherein the top structure comprises at least one sealing element for realizing a substantially medium-tight seal between at least one closing element and at least one analysis compartment connecting to the at least one closing element.

12. The system as claimed in claim 11, wherein the top structured is configured to engage substantially medium-tightly on a closing body of the closing element around an analysis opening arranged in the closing body.

13. The system as claimed in claim 8, wherein the device comprises at least one heating element for heating the biological sample received in at least one container.

14. The system as claimed in claim 13, wherein the device comprises at least one fan for blowing heat generated by the at least one heating element in the direction of the at least one container.

15. The system as claimed in claim 8, wherein the device is manufactured from a thermally insulating material.

16. The system as claimed in claim 8, wherein the device comprises at least one processor for controlling the device.

17. The system as claimed in claim 8, wherein the device comprises means for causing movement of the sample.

18. The system as claimed in claim 8, wherein the device comprises at least one preconcentrator for temporarily binding at least one chemical compound coming from the sample.

19. A method for analysing samples, by making use of an assembly of a container for a biological sample and the closing element, as claimed in claim 1, connected to the container, comprising the steps of:
   A) providing an assembly of a container and a closing element connected to the container,
   B) injecting a biological sample via at least one penetrable element of the closing element into the container,
   C) having at least one ventilating channel of the closing element connect in substantially medium-tight manner to at least one analysis compartment provided with at least one chemical trace detector,
   D) allowing metabolic gas formed in the container to displace via the ventilating channel and a bacterial filter of the closing element into the analysis compartment, and
   E) at least partially analysing the metabolic gas in the analysis compartment with at least one chemical trace detector.

20. The method as claimed in claim 19, further comprising the step of heating for a period of time the biological sample injected into the container.

* * * * *

UNITED STATES PATENT AND TRADEMARK OFFICE
CERTIFICATE OF CORRECTION

PATENT NO. : 11,123,737 B2
APPLICATION NO. : 16/101985
DATED : September 21, 2021
INVENTOR(S) : Albert Bos Page 1 of 1

It is certified that error appears in the above-identified patent and that said Letters Patent is hereby corrected as shown below:

In the Claims

Column 14, Line 44, Claim 10, delete "releasably," and insert -- releasably --

Column 14, Line 51, Claim 12, delete "structured" and insert -- structure --

Column 15, Line 5, Claim 19, delete "samples," and insert -- samples --

Signed and Sealed this
Twenty-fifth Day of January, 2022

Drew Hirshfeld
*Performing the Functions and Duties of the*
*Under Secretary of Commerce for Intellectual Property and*
*Director of the United States Patent and Trademark Office*